United States Patent [19]

Isshiki et al.

[11] Patent Number: 5,344,972

[45] Date of Patent: Sep. 6, 1994

[54] PROCESS FOR PRODUCING ACETIC ACID

[75] Inventors: Tomiya Isshiki, Tokyo; Yasuhiko Kijima, Matsudo; Takayuki Watanabe, Funabashi, all of Japan

[73] Assignee: Mitsubishi Gas Chemical Company, Inc., Tokyo, Japan

[21] Appl. No.: 400,106

[22] Filed: Jul. 20, 1982

Related U.S. Application Data

[63] Continuation of Ser. No. 211,741, Dec. 1, 1980, abandoned.

[30] Foreign Application Priority Data

Dec. 13, 1979 [JP] Japan ................... 54-161934

[51] Int. Cl.$^5$ ............................. C07C 51/12
[52] U.S. Cl. ..................................... 562/517
[58] Field of Search .......................... 562/517

[56] References Cited

U.S. PATENT DOCUMENTS

| Re. 29,981 | 5/1979 | Isogai | 562/607 |
| 3,839,428 | 10/1974 | Isogai | 562/517 |
| 4,194,056 | 3/1980 | Antoniades | 562/517 |

FOREIGN PATENT DOCUMENTS

| 2109025 | 9/1971 | Fed. Rep. of Germany | 562/607 |
| 3025373 | 9/1973 | Japan . | |
| 3061373 | 9/1973 | Japan . | |
| 351374 | 1/1974 | Japan . | |
| 6570376 | 6/1976 | Japan . | |
| 628161 | 8/1949 | United Kingdom . | |
| 1286224 | 8/1972 | United Kingdom | 562/607 |

OTHER PUBLICATIONS

Roth et al, Low Pressure Process for Acetic Acid via Carbonylation, Chem. Tech., Oct. 1971, pp. 600-605.
Fenton et al, Noble Metal Ions⇌Noble Catalysts, Chem. Tech., Apr. 1972, pp. 220-225.

Primary Examiner—José G. Dees
Assistant Examiner—Joseph M. Conrad
Attorney, Agent, or Firm—Jacobson, Price, Holman & Stern

[57] ABSTRACT

There is disclosed a process for producing acetic acid in which methyl formate is isomerized into acetic acid with a catalyst containing at least one of Pd, Ru and Ir, at least one compound of said metals or a mixture thereof, and a promoter of a halide compound in the presence of carbon monoxide. This process can be carried out under mild reaction conditions and acetic acid is obtained in high yield.

14 Claims, No Drawings

PROCESS FOR PRODUCING ACETIC ACID

This is a continuation of application Ser. No. 211,741 filed Dec. 1, 1980, now abandoned.

This invention relates to a process for producing acetic acid by isomerization of methyl formate, in particular to a process for producing acetic acid which comprises contacting methyl formate with a catalyst system comprising at least one metal of palladium, ruthenium and iridium, at least one compound of said metals or a mixture thereof and a promoter of a halide compound in the presence of carbon monoxide.

Catalytic production of acetic acid from methyl formate has already been known in which the catalyst is iron, cobalt or nickel (British Patent 628161, Japanese Patent Publication 30613/73 and Japanese Patent Publication 30253/73), rhodium (Japanese Patent Publication 3513/74) or rhenium (Japanese Patent Public Disclosure 65703/76). With the use of iron, cobalt, nickel or rhenium catalyst, the reaction pressure is within an acceptable range of about 300 Kg/cm² G but there is often observed low conversion and the formation of undesirable byproducts such as formic acid, methane and methyl acetate thereby rendering such process inpractical. Recently, a process using rhodium catalyst was proposed. This process makes it possible to use more mild reaction conditions and obtain acetic acid with much less byproducts. However, this process involves various disadvantages, for example, rhodium is very expensive [Hydrocarbon process 54, June 83 (1975)], and in commercial practice, precautions must be taken to prevent reduction of a rhodium complex into metallic rhodium under reductive atmosphere [Kagaku to Kogyo 29, 5, 376 (1975)] and to prevent escape of rhodium caused by evaporation during distillation operation of the reaction product (Japanese Patent Public Disclosure 90204/78).

In view of the above, the inventors have conducted intensive investigation of various metal compounds for finding out a catalyst system useful for isomerization of methyl formate into acetic acid and we have found a novel catalyst system with which isomerization of methyl formate can be carried out effectively. According to this invention, therefore, there is provided a process for producing acetic acid which comprises contacting methyl formate at an elevated temperature with a catalyst system comprising at least one metal of palladium, rhenium and iridium, at least one compound of said metals or a mixture thereof and a promoter of a halide compound in the presence of carbon monoxide. According to this invention, unexpectedly mild conditions can be employed under which isomerization of methyl formate is effected and a surprisingly high yield of acetic acid can be obtained; such advantages are demonstrated upon comparing the reaction conditions and the yield of the product according to this invention with those of prior art, for example, Japanese Patent Public Disclosures 65703/76 and 29710/73. The former process is carried out using a metallic rhenium catalyst at a reaction temperature and under a reaction pressure comparable with those of this invention, but the conversion of methyl formate and the yield of acetic acid are inferior. The latter employs a catalyst system supported on activated carbon and severe reaction conditions, such as, at a temperature of above 300° C., but the yield of acetic acid is as low as about 30%.

Therefore, it is surprising that a combination of a promoter of halide compound with at least one catalytic ingredient and selection of the catalytic ingredient of at least one metal of palladium, ruthenium and iridium, at least one compound of said metals or a mixture thereof have a remarkable effect on the reaction to give a high yield of acetic acid which cannot be expected from the prior art. As mentioned above, according to this invention, with the presence of carbon monoxide, the combination of a promoter of a halide compound with the catalytic ingredient and the selection of relatively inexpensive catalytic ingredient, acetic acid can be produced in high yield from methyl formate. In particular, palladium and ruthenium catalysts are commercially available at lower price than a rhodium catalyst [Yuki Gosei Kagaku Kyokaishi 35, 152 (1978)] and therefore they are preferred from the economical point of view.

The palladium, ruthenium or iridium catalyst can be used in any form of zero valence state and any higher valence state. For example, they can be used in finely divided particles of the metal and in a metal compound such as, a carbonate, an oxide, a hydroxide, a nitrate, a chloride, a bromide, an iodide and, a carboxylate of an alkanoic acid having 1 to 20 carbon atoms. A metal complex is also used including a metal carbonyl, such as, ruthenium carbonyl and iridium carbonyl, a metal carbonyl halide, such as, tricarbonyl iridium chloride, $[Ir(CO_3)Cl]_2$, and an acetyl acetonate, such as, palladium acetyl acetonate $Pd(C_5H_7O_2)_2$ and the like.

Following are example of the metal compounds which can be employed in this invention.

$PdX_2$, $[Pd(CO)X_2]_2$, $[Pd(Pph_3)_2]X_2$, $[Pd(Pph_3)]_2(CO)Br$, $[PdX_4][(n-C_4H_9)_4P]$, $Pd[(n-C_4H_9)_3P](CO)Cl_2$, $PdCl(Pph_3)_2(SnCl_3)$, $Pd[(n-C_4H_9)_3P]_2I_2$, $RuX_3$, $RuX_3.3H_2O$, $Ru(CO)_2I_2$, $Ru_3(CO)_{12}$, $RuCl_2(CO)(Pph_3)_3$, $RuI_2(CO)(Asph_3)_3$, $RuBr_2(CO)[(n-C_4H_9)_3P]_3$, $RuBr_3(CO)(Pph_3)_2$, $K_2[Ru_2(SnCl_3)_2]$, $K_4Ru_2X_2(SnX_3)_4$, $IrX_3$, $IrX_3.3H_2O$, $Ir_2(CO)_4X_2$, $Ir_2(CO)_8$, $Ir(Pph_3)_2(CO)X$, $Ir(Pph_3)_2(C-H_3I)_2Ir(SnCl_3)(Pph_3)_3$, $IrCl(CO)(Asph_3)_2$, $IrI(CO)(Sbph_3)_2$, $[Ir(CO)_2X_2][(n-C_4H_9)_4N]$, $[Ir_2(CO)_2X_4][(n-C_4H_9)_2As]$, $[Ir(CO)_4][(n-C_4H_9)_4P]$, $Ir(Pph_3)_2(CO)Br$, $Ir[(n-C_4H_9)_3P]_2(CO)Br$, $Ir[(n-C_4H_9)_3P]_2(CO)I$, $IrX(Pph_3)_3$, $IrCl(Pph_3)_3H_2$, $Ir(Pph_3)_3H(CO)$, $[Ir(C_2H_4)_2Cl]_2$ and $K_4Ir_2X_2(SnX_3)_4$, wherein X represents Cl, Br and I and ph represents phenyl ($C_6H_5$-).

In the reaction according to this invention, the presence of at least one catalytic ingredient and a promoter of a halide compound is essential. A suitable halide is a bromide, an iodide or a mixture thereof, preferably an iodide; in general the halide is a methyl halide, an acetyl halide, a hydrogen halide or a mixture thereof, and they can be directly added to the reaction mixture. Any compound which is capable of forming the halide mentioned above in the reaction mixture by reacting with another component, such as, methyl formate, methyl acetate, methanol and the like, can also be used and such compounds include an inorganic halide, such as, an alkali metal halide and an alkaline earth metal halide, and an elementary halogen, such as, iodine and bromine.

According to this invention, the reaction can proceed effectively with the combination of the catalytic ingredient and the promoter mentioned above; in order to accelerate the reaction rate, an organic and/or inorganic secondary promoter can be incorporated. An organic secondary promoter is preferred. The organic secondary promoter can be introduced together with the reactant to the reaction system. Alternatively, the secondary promoter is bonded with the catalyst metal to form a metal complex which is then introduced in the system.

The preferred organic secondary promoter includes an organic compound containing nitrogen, phosphorus, antimony or arsenic atom. The effective organic secondary promoters are classified and exemplified as follows without intention to be limited thereto.

I. Trivalent compounds

A. Organic compounds represented by the formula

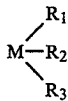

wherein M represents N, P, Sb or As.

(a) In the formula, $R_1$, $R_2$ and $R_3$ may be the same or different, and each represents hydrogen, an alkyl having 1 to 10 carbon atoms, a cycloalkyl or an aryl.

Compounds wherein M is N include ammonia and amines, such as, mono-(di- or tri-) methylamine, mono-(di- or tri-) ethylamine, dimethylethylamine, tri-n-(or i-) propylamine, tri-n-(or t-) butylamine, aniline, dimethyl- (or diethyl-) aniline, dimethylbenzylamine, toluidine, cyclohexylamine and the like.

Compounds wherein M is P include phosphines, such as, tri-n-(or i-) propylphosphine, tri-n-(or t-) butylphosphine, tricyclohexylphosphine, triphenylphosphine and the like.

Compounds wherein M is Sb include stibines, such as, tri-i-propylstibine, ethyl-di-i-propylstibine, triphenylstibine, tri-o-tolylstibine, phenyldiamylstibine and the like.

Compounds wherein M is As include arsines, such as, trimethylarsine, triethylarsine, tricyclohexylarsine, phenyl-di-i-propylarsine, diphenylarsine and the like.

(b) In the formula, $R_1$ represents hydrogen, an alkyl having 1 to 10 carbon atoms, a cycloalkyl or an aryl and $R_2$ and $R_3$ together form a polymethylene having 1 to 5 carbon atoms.

Compounds include heterocyclic compounds, such as, pyrrolidine, N-methylpyrrolidine, piperidine, N-phenylpiperidine and the like.

(c) In the formula, $R_1$ and $R_2$ may be the same or different and each represents hydrogen, an alkyl having 1 to 10 carbon atoms, a cycloalkyl or an aryl and $R_3$ represents a saturated aliphatic acyl having 1 to 10 carbon atoms, or $R_1$ represents hydrogen, an alkyl having 1 to 10 carbon atoms, a cycloalkyl or an aryl and $R_2$ and $R_3$ together form a carboxypolymethylene.

Compounds include amides, such as, acetamide, N,N-dimethylacetamide, acetanilide, N-methyl, N-phenylaceyamide and the like and lactams, such as, N-methylpyrrolidinone.

(d) In the formula, $R_1$, $R_2$ and $R_3$ may be the same or different and at least one is carboxymethyl and the others are hydrogen, an alkyl having 1 to 10 carbon atoms, a cycloalkyl or an aryl.

The compounds include carboxylic derivatives, such as, N,N-dimethylglycine, N,N-diethylglycine, iminodiacetic acid, N-methyliminodiacetic acid, nitrilotriacetic acid and the like.

B. Organic compounds represented by the formula

wherein R represents an alkyl having 1 to 10 carbon atoms, a cycloalkyl or an aryl.

Compounds include nitriles, such as, acetonitrile, propionitrile, benzonitrile and the like.

C. Organic compounds are represented by the formula

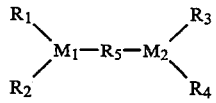

wherein $M_1$ and $M_2$ may be the same or different and each represents N, P, Sb or As.

(a) In the formula, $R_1$, $R_2$, $R_3$ and $R_4$ represent hydrogen an alkyl having 1 to 10 carbon atoms, a cycloalkyl or an aryl and $R_5$ represents a polymethylene having 1 to 10 carbon atoms, a phenylene or carbonyl.

Compounds wherein $M_1$ and $M_2$ are N, P, Sb or As include ethylene bis(diphenylphosphine), phenylene bis(dimethylphosphine), bis(diphenylarsino)ethane, bis(di-i-propylarsino) hexane, bis(diethylstibino)pentane, N,N,N',N'-tetramethylethylenediamine, N,N,N',N'-tetraethylethylenediamine, N,N,N',N',-tetra-n-propylethylenediamine, N,N,N',N'-tetramethylmethylenediamine, N,N,N',N'-tetramethylurea, N-methyl-2-pyrrolidinone and the like.

(b) In the formula, $R_1$ and $R_3$ represent hydrogen, an alkyl having 1 to 10 carbon atoms, a cycloalkyl or an aryl, $R_2$ and $R_4$ together form a polymethylene having 1 to 5 carbon atoms and $R_5$ represents a polyalkylene having 1 to 5 carbon atoms.

Compounds include heterocyclic compounds, such as, piperazine, N-methylpiperazine, 2-methyl-N,N'-dimethylpiperazine and the like.

(c) Other compounds represented by the formula include, for example, tris(diethylaminomethyl)stibine, 2,5-dicarboxypiperazine, cyclohexane-1,2-diamine-N,N,N',N'-tetraacetic acid and salts and tetramethylester thereof, ethylenediamine tetraacetic acid and salts and tetramethyl ester thereof, 1,4-azabicyclo[2,2,2]octane, methyl substituted 1,4-diazacyclo[2,2,2]octane, adiponitrile, N-methylmorphorine and the like.

II. Heterocyclic compounds

Useful heterocyclic compounds include, for example, pyrrole, pyrroline, pyridine, pyrimidine, pyrazole, pyrazoline, pyridazine; picolines, such as, α-(β- or γ-)picoline; lutidines, such as 2,4-(or 2,6-)lutidine; collidines, such as, 2,4,6-collidine; benzotriazole, 2,2'-dipyridyl and derivatives thereof, such as, 4,4'-dimethyl-2,2'-dipyridyl, 4-triethylsilyl-2,2'-dipyridyl; purine; pyridine derivatives, such as, α-(or β-) aminopyridine, 2-hydroxypyridine, methyl substituted 2-hydroxypyridine, picolinic acid, methyl substituted picolinic acid, 2, 6-dicarboxy pyridine, 2-(dimethyl-amino) pyridine; imidazole, 1, 10-phenanthroline and derivatives thereof, such as, 4-chloro-1, 10-phenanthroline, 5-(thiabenzyl)-1, 10-phenanthroline; quinoline and derivatives thereof, such as, 2-(dimethylamino)-6-methoxyqinoline, 8-hydroxyquinoline and 2-carboxyquinoline.

III. Pentavalence nitrogen compounds

Ammonium acetate, ammonium propionate and triphenyl phosphine iminium chloride are also useful as a secondary promoter. Of these, the most preferred secondary promoter is nitrogen- or phosphorus-containing organic compounds, especially trivalent phosphorus compounds. An effective inorganic secondary promoter is a metal having an atomic weight of from 6 to 120 and belonging to groups IA, IIA, IIIA, IVA, IB, IIB, VB, VIB and VIIB of the Periodic Table and a compound of said metals. The preferred metals are lithium, sodium, potassium, magnesium, calcium, aluminum, tin, zinc, cadmium, copper, manganese, chromium and vanadium. The inorganic secondary promoter can be used in an elemental form, for example, finaly divided metal particles. However, if the reaction conditions allows, a cation form of the promoter, such as, an organic or inorganic metal compound, can be introduced into the reaction system and used advantageously. Typical compounds include an oxide, a hydroxide, a halide, preferably bromide and iodide, an oxyhalide, a hydride, a carbonyl, an alkoxide, a nitrate, a nitrite, a phosphate, a phosphite, an aliphatic, alicyclic, napthenic, aryl-aliphatic or aromatic carboxylate, such as, an acetate, a butylate, a decanate, a laurylate, a stearate and a benzoate. Other preferred compounds are, for example, an alkyl metal, a chelate compound, an association compound and an enolate. A bromide, an iodide and an organic acid salt, such as, an acetate are most preferred as a secondary promoter. Both inorganic and organic secondary promoters may be combined with the catalytic ingredient of metal, and such combination is often advantageous under certain conditions.

The concentration of the catalytic ingredient of palladium, ruthenium and irridium in the liquid reaction medium is, in terms of metal, $10^{-6}$ to 5 M/l, preferably $10^{-4}$ to 4 M/l and more preferably $10^{-3}$ to 2 M/l.

The concentration of the promoter of the halide compound is, in terms of halogen atom, $10^{-6}$ to 15 M/l, preferably $10^{-5}$ to 5 M/l and more preferably $10^{-4}$ to 3 M/l.

The concentration of the secondary promoter may vary depending upon the concentration of the catalytic ingredient, and, in general, ranges within $10^{-6}$ to 10 M/l, preferably $10^{-4}$ to 5 M/l and more preferably $10^{-3}$ to 2.5 M/l.

The temperature at which isomerization is effected is 20° to 500° C., preferably 80° to 350° C. and more preferably 100° to 250° C. The total pressure of the reaction system is not critical, as long as the pressure is sufficiently high to maintain the reaction medium in a liquid phase and the partial pressure of carbon monoxide is within an appropriate range.

From the theoretical point of view, carbon monoxide does not participate in isomerization of methyl formate into acetic acid according to this invention:

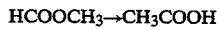

$$HCOOCH_3 \rightarrow CH_3COOH$$

In order to prevent decomposition of methyl formate and smoothly proceed the isomerization, it is essential to having carbon monoxide in the reaction system.

In general, the partial pressure of carbon monoxide is 0.5 to 350 atm. (7.35 to 5,145 psi), preferably 1 to 300 atm. (14.7 to 4,410 psi) and more preferably 3 to 250 atm. (44.1 to 3,675 psi). However a wider range of 0.05 to 1,000 atm. (0.74 to 14,700 psi) may be employed.

Methyl formate can be produced without using petrochemicals such as ethylene as starting material. For example, the formate is produced by reacting methanol and carbon monoxide in the presence of an alcoholate of an alkali metal or an alkaline earth metal, or by subjecting methanol to dehydrogenation in the presence of a copper compound catalyst (Japanese Patent Publications 46819/78, 4681/78 and 128315/78). The presence of impurities, such as, methanol and dimethyl ether in the methyl formate is acceptable, provided that they do not adversely affect the overall isomerization reaction.

In general, methyl formate and carbon monoxide contain a certain amount of water. However, the amount of water present in the methyl formate commercially available and carbon monoxide is acceptable. However, note that a large excess of water causes decomposition of methyl formate; therefore the water content of each material is to be limited to less than 10 mol %, preferably less than 5 mol % and more preferably less than 3 mol %. Since the isomerization does not produce water, the desired level of water in the reaction system is maintained by drying the starting materials and the reaction medium.

Methyl formate is a solvent for the acetic acid product and the catalyst system, so a solvent is not necessarily required. However, the use of a solvent is desirable. Examples of suitable solvent include; an organic acid, such as, acetic acid, propionic acid, butyric acid, octanoic acid, phthalic acid and benzoic acid; an organic ester, such as, methyl acetate, ethyl acetate, ethylene glycol diacetate, propylene glycol diacetate, dimethyl adipate, methyl benzoate, ethyl benzoate, diemthyl phthalate, diethyl phthalate, dioctyl phthalate, phenyl acetate and tolyl acetate; a hydrocarbon, such as, dodecane, hexadecane, benzene, toluene, xylene, naphthalene and biphenyl; an inorganic ester, such as, triphenyl phosphate, tricresyl phosphate, dibutyl phenyl phosphate and tetramethyl orthosilicate; a phenol, such as, phenol, cresol, chlorophenol and nitrophenol; and a ketone, such as, acetone, methyl ethyl ketone, dibutyl ketone, methyl i-butyl ketone, acetophenone and benzophenone.

Since this invention relates to the production of acetic acid, the most preferred solvent is acetic acid, methyl acetate or a mixture thereof. Such solvents have the additional advantage of tendency to stabilize the methyl formate starting material and the catalyst system under the reaction conditions.

The process according to this invention can conveniently be carried out in a liquid phase. A gas phase reaction may also be employed. In the gas phase reaction, a catalyst system comprising at least one active component of palladium, ruthenium and iridium deposited on a support, such as, active carbon, alumina, silica gel, silica-alumina, magnesia and a molecular sieve, is packed in a reaction tube through which gaseous methyl formate, carbon monoxide and a halide compound are passed to effect isomerization.

The reaction product can be subjected to separation and purification, for example, distillation. The starting material employed in this invention is methyl formate which is an ester and, therefore, the reaction system can be maintained in substantially anhydrous state. This makes it possible to obtain the acetic acid product in as high a concentration as possible near glacial acetic acid without removing water.

This invention will be illustrated in further detail by means of the following examples. However, it should be understood that this invention is in no way limited to these examples.

EXAMPLE 1

A 300 ml tantalum autoclave equipped with a magnetic stirrer was charged with 90 g of methyl formate, 2.56 g of palladium acetate, 14.2 g of methyl iodide and 11.9 g of triphenyl phosphine, and carbon monoxide was supplied thereto at room temperature until a pressure of 50 atm. was established. Then, the reaction was carried out at 200° C. for 180 minutes.

After cooling, the reaction mixture was removed and a portion thereof was analyzed by gas chromatography. It was found that 85.8 g of acetic acid was produced, the yield being 95.3%.

EXAMPLE 2

Procedures similar to those of Example 1 were followed excepting that 30 g of methyl formate and, as solvent, 30 g of acetic acid and 30 g of methyl acetate, instead of 90 g of methyl formate, were used.

The amount of acetic acid produced from the formate was 29.2 g, the yield being 97.4%.

EXAMPLE 3

Procedures similar to those of Example 1 were followed excepting that 30 g of methyl formate and 60 g of methyl acetate, instead of 90 g of methylcformate, were used.

The amount of acetic acid in the reaction product was 29.0 g, the yield being 96.7%.

EXAMPLE 4

Using 2.38 g of palladium chloride, the procedures of Example 3 were repeated. 29.4 Grams of acetic acid was produced, the yield being 97.9%.

EXAMPLE 5

The autoclave employed in Example 1 was charged with 90 g of methyl formate, 8.0 g of dichloro-bis(triphenylphosphine) palladium, 7.1 g of methyl iodide and 6.7 g of lithium iodide.

Then, carbon monoxide was supplied to the autoclave until the pressure reached 35 atm. at room temperature. The reaction was carried out at 190° C. for 200 minutes to obtain 80.5 g of acetic acid (yield: 89.4%).

EXAMPLE 6

As palladium compound, 2.56 g of dichloro bis(benzonitrile)palladium and, as iodine compound, 14.2 g of calcium iodide were used and the procedures of Example 3 were repeated. The reaction product contained 29.5 g of acetic acid (yield: 98.3%).

EXAMPLE 7

To the autoclave of Example 1 was charged 30 g of methyl formate, 0.163 g of iridium chloride, 14.2 g of methyl iodide, 0.572 g of triphenylphosphine, 60 g of methyl acetate, as solvent, and synthesis gas (CO/H$_2$ 60/40 vol %) at 25 atm. and room temperature. The mixture was heated at 200° C. for 120 minutes to effect isomerization. The amount of acetic acid produced was found to be 4.8 g (yield: 16%).

EXAMPLE 8

To the autoclave of Example 1 was charged 30 g of methyl formate, 0.415 g of ruthenium acetylacetonate, 14.2 g of methyl iodide, 1.09 g of triphenylphosphine, 60 g of acetic acid, as solvent, and synthesis gas (CO: 50 vol %) at 20 atm. and room temperature. The reaction was carried out at 185° C. for 60 minutes. The amount of acetic acid obtained from methyl formate was 10.8 g (yield: 36.0%).

EXAMPLE 9

In the autoclave employed in Example 1, 30 g of methyl formate was isomerized in the presence of 2.08 g of ruthenium acetylacetonate, 14.2 g of methyl iodide, 4.2 g of tri-n-butylphosphine, 60 g of methyl acetate and synthesis gas (CO:50 vol %) at 20 atm. and room temperature. The reaction was carried out at 185° C. for 90 minutes. In the resulting mixture, 26.3 g of acetic acid was obtained (yield: 87.7%).

EXAMPLE 10

Methyl formate (30 g), dichloro bis(triphenyl phosphine) palladium (8.0 g), methyl iodide (14.2 g), 2, 6-lutidine (0.45 g) and methyl acetate (60 g), as solvent, were changed into the autoclave of Example 1 to which carbon monoxide was introduced until a pressure of 35 atm. at room temperature was established. The reaction mixture was heated at 200° C. for 180 minutes. Acetic acid produced amounted 29.6 g corresponding to a yield of 98.7%.

EXAMPLE 11

Procedures similar to those of Example 1 were repeated excepting that 1.18 g of palladium black powder available from Nippon Engelhald Co., Ltd. Tokyo, Japan was used instead of 2.56 g of palladium acetate.

The resultant mixture contained 54.4 g of acetic acid, the yield being 60.4%.

EXAMPLE 12

An autoclave used in Example 1 was charged with 90 g of methyl formate, 8.74 g of 5% palladium supported on activated carbon available from Nippon Engelhald Co., Ltd., 14.2 g of methyl iodide, 11.9 g of triphenylphosphine and carbon monoxide at 60 atm. and room temperature. The reaction was carried out at 230° C. for 180 minutes. Acetic acid produced was 60.4 g (yield: 67.2%).

What is claimed is:

1. A process for producing acetic acid which comprises contacting methyl formate with a catalyst system consisting essentially of at least one catalytic ingredient selected from the group consisting of metallic palladium, a palladium compound and a mixture thereof, a primary promoter comprising a halide compound having a concentration of $10^{-6}$ to 15 M/l in terms of halogen atom and a secondary promoter comprising an organic trivalent phosphorus compound in the presence of carbon monoxide having a partial pressure of 3 to 250 atm and in the presence of at least one solvent selected from the group consisting of acetic acid and methyl acetate at a temperature of from 100° to 250° C.

2. A process for producing acetic acid in accordance with claim 1, wherein the catalytic ingredient is at least one compound selected from the group consisting of a carbonate, an oxide, a hydroxide, a nitrate, a bromide, an iodide, a chloride, a salt of an alkanoic acid having 1 to 20 carbon atoms and a complex of palladium.

3. A process for producing acetic acid in accordance with claim 1, wherein said halide compound is at least one compound selected from the group consisting of methyl halide, an acetyl halide, and a hydrogen halide.

4. A process for producing acetic acid in accordance with claim 1, wherein said halide compound is an inorganic halide compound capable of forming a methyl halide, an acetyl halide or a hydrogen halide in the reaction medium, and iodine and bromine.

5. A process for producing acetic acid in accordance with claim 3, wherein said halide compound is an iodide, bromide or a mixture thereof.

6. A process for producing acetic acid in accordance with claim 1, wherein said halide compound is iodine.

7. A process for producing acetic acid in accordance with claim 1, wherein the concentration of the catalytic ingredient is, in terms of elemental metal, $10^{-6}$ to 5 M/l.

8. A process for producing acetic acid in accordance with claim 7, wherein said concentration is $10^{-4}$ to 4 M/l.

9. A process for producing acetic acid in accordance with claim 7, wherein said concentration is $10^{-3}$ to 2 M/l.

10. A process for producing acetic acid in accordance with claim 1, wherein said concentration is $10^{-5}$ to 5 M/l.

11. A process for producing acetic acid in accordance with claim 1, wherein said concentration is $10^{-4}$ to 3 M/l.

12. A process for producing acetic acid in accordance with claim 1, wherein the concentration of the secondary promoter is $10^{-6}$ to 10 M/l.

13. A process for producing acetic acid in accordance with claim 12, wherein said concentration is $10^{-4}$ to 5 M/l.

14. A process for producing acetic acid in accordance with claim 12, wherein said concentration is $10^{-3}$ to 2.5 M/l.

* * * * *